United States Patent [19]

Bristol et al.

[11] 4,409,226

[45] Oct. 11, 1983

[54] IMIDAZO[1,5-A]PYRIDINES

[75] Inventors: James A. Bristol, Ann Arbor, Mich.; Raymond G. Lovey, West Caldwell, N.J.

[73] Assignee: Schering Corporation, Kenilworth, N.J.

[21] Appl. No.: 308,349

[22] Filed: Oct. 5, 1981

[51] Int. Cl.³ .................... A61K 31/44; C07D 471/04
[52] U.S. Cl. .................. 424/256; 424/248.5; 424/248.52; 424/248.54; 424/248.55; 544/127; 546/121
[58] Field of Search .................. 546/121; 544/127; 424/248.52, 256, 248.54, 248.55, 248.5

[56] References Cited

U.S. PATENT DOCUMENTS

| | | | |
|---|---|---|---|
| 3,790,586 | 2/1974 | Irikura et al. | 546/121 |
| 4,044,015 | 8/1977 | Kuhla et al. | 424/263 |
| 4,228,291 | 10/1980 | Durant et al. | 424/269 |
| 4,307,101 | 5/1977 | Durant et al. | 424/263 |
| 4,307,101 | 12/1981 | Durant et al. | 424/278 |

OTHER PUBLICATIONS

Blatcher et al., Tet. Letters, vol. 21, pp. 2195–2196, Jun. 1980.
Glover et al., J.E.S. Perkin I, 959 (1980).
Fuentes et al., C.A. 83, 131521g (1975).
Glover et al., C.A. 80, 47900k (1974).
Aleksandrova et al., C.A., 76, 139814f (1972).

*Primary Examiner*—Henry R. Jiles
*Assistant Examiner*—Bernard Dentz
*Attorney, Agent, or Firm*—Gerald S. Rosen; Bruce M. Eisen

[57] ABSTRACT

The invention relates to imidazo[1,5-a]pyridine derivatives which are useful in the treatment of peptic ulcer diseases.

29 Claims, No Drawings

IMIDAZO[1,5-A]PYRIDINES

SUMMARY OF THE INVENTION

This invention relates to certain substituted imidazo[1,5-a]pyridine compounds and pharmaceutical compositions and formulations thereof, novel processes and intermediates for making said compounds, and methods of treating peptic ulcer disease utilizing said compounds.

More particularly, this invention relates to imidazo[1,5-a]pyridine compounds represented by the following structural formulas I and II:

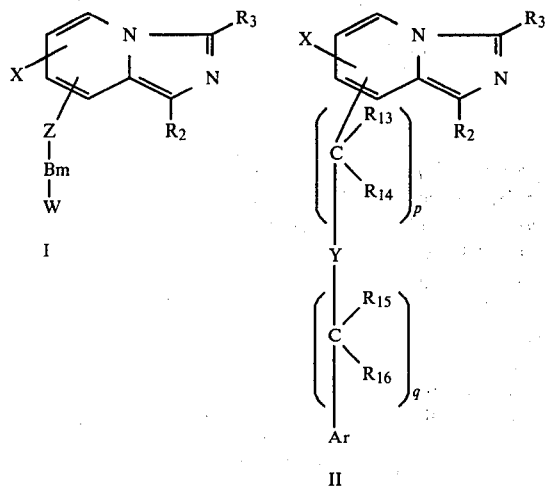

the 5,6,7,8-tetrahydro and perhydro derivatives thereof, and the pharmaceutically acceptable salts thereof, wherein:

$R_2$ and $R_3$ each independently represent hydrogen, lower alkyl, trifluoromethyl, B-CF$_3$, B-Ar, Ar, halogen, B-halogen, B-OR$_8$, B-S(O)$_n$-lower alkyl, wherein (n) is 0, 1, or 2;

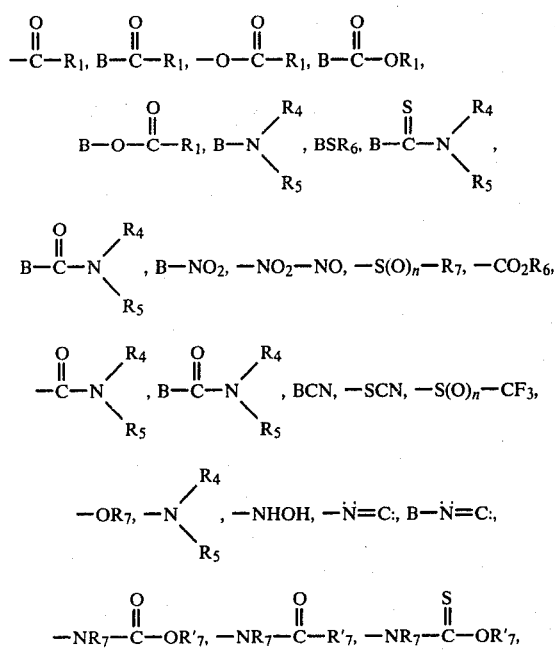

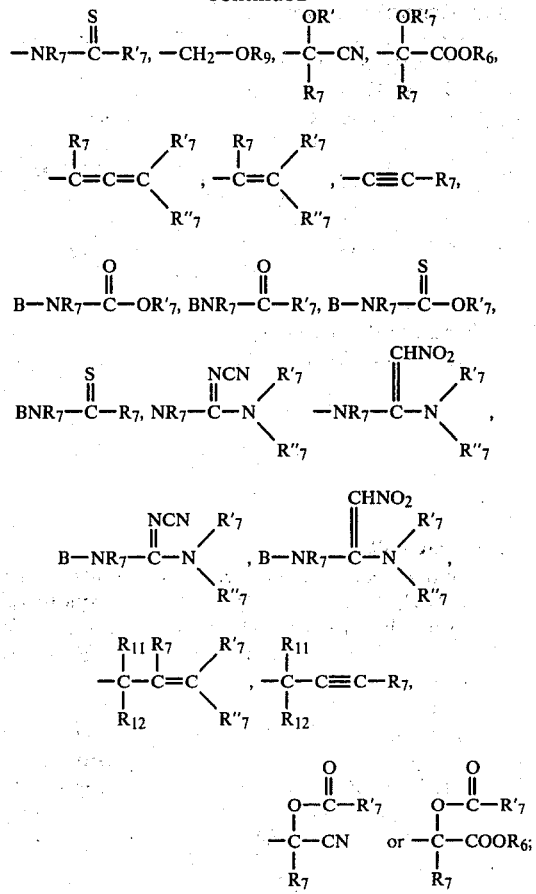

or a straight- or branched-chain alkenyl or alkynyl group having 2 to 6 bridging carbon atoms and aryl-substituted derivatives thereof;

X represents hydrogen, lower alkyl, halogen, hydroxy, lower alkoxy, trifluoromethyl,

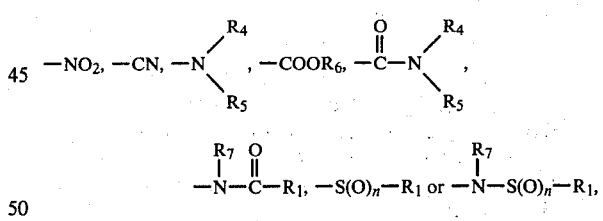

wherein n is zero, one or two with the proviso that when R$_1$ represents

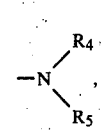

n represents two;

Z represents —O, —S, —SO, —SO$_2$, —NR$_6$, or a bond connecting B to the 5, 6, 7, or 8-position of the imidazo [1,5-a]pyridine nucleus;

B represents a straight- or branched-chain lower alkylene moiety;

Bm represents a straight- or branched-chain lower alkylene moiety and, when Z is a bond connecting Bm and the imidazo[1,5-a]pyridine nucleus, the —OR$_7$ derivatives thereof or the α(β)— or the β(γ)— unsaturated derivatives thereof;

m is zero to 10 with the proviso that when W is Ar, m is not zero and the number of bridging carbons between Z and W is no greater than 5.

W represents Ar wherein Ar represents phenyl, pyridyl, thienyl, imidazolyl, furanyl or X'—, Y'—, Z'— substituted-phenyl wherein each of X'—, Y'— and Z'— independently is as hereinabove defined for X; and when m is 1 to 3, W represents alkenyl, alkynyl, $Z^1R_6$ or $Z^1COR_6$, wherein $Z^1$ is —O—, —S—, —SO, —$SO_2$ or —$NR_6$;

Y represents O, S, SO, $SO_2$ or $NR_6$;

wherein in the above definitions:

$R_1$ represents Ar, lower alkyl,

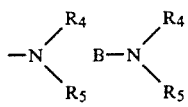

or Ar-loweralkyl;

$R_4$ and $R_5$ each independently represents hydrogen, lower alkyl, Ar, ar-loweralkyl, loweralkoxyloweralkyl, trifluoromethyl loweralkyl, or when taken together with the nitrogen atoms to which they are attached represents a 4–7 membered cyclic amino or a morpholino group;

$R_6$ represents hydrogen, $C_1$- to $C_{12}$- alkyl, aryl or an arylalkyl group having up to 12 carbon atoms;

$R_7$, $R_7'$ and $R_7''$ each independently represents hydrogen or loweralkyl;

$R_8$ represents hydrogen, loweralkyl, loweralkoxyloweralkyl, trifluoromethylloweralkyl, Ar-loweralkyl, or Ar;

$R_9$ represents

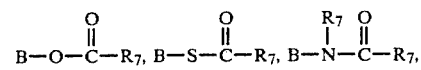

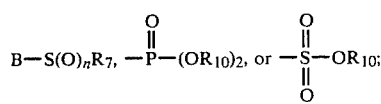

$R_{10}$ represents H, alkali metal or lower alkyl;

$R_{11}$ and $R_{12}$ each independently represents hydrogen or lower alkyl or together represent oxygen;

$R_{13}$ and $R_{14}$ each independently represents H, alkyl, aryl, or together represent —O— or —S—;

$R_{15}$ and $R_{16}$ each independently represents H, alkyl, aryl, or together represent —O— or —SD—, provided that when $R_{13}$ and $R_{14}$ together represent —O— or —S— $R_{15}$ and $R_{16}$ do not represent —O— or —S—;

p and q are each independently 0, 1 or 2 provided that when one of p and q is zero, the other is not zero.

As employed throughout this specification, the term "halogen" refers to fluoro, chloro, bromo and iodo, with chloro and fluoro being preferred. The term "lower", as it modifies such radicals as alkyl, alkylene, alkoxy and the like includes straight and branched-chain radicals having up to six carbon atoms, e.g. methyl, ethyl, propyl, butyl, t-butyl, isopropyl, neopentyl, dimethylbutyl and the like. Methyl is the preferred lower alkyl and is especially preferred at $R_2$ and/or $R_3$ in Formulas I and II. The radical BCN is most preferably —$CH_2CN$, particularly at $R_2$. The term "pyridyl" includes the 2-, 3-, and 4-isomers, and their halogen and lower alkyl substituted analogs; the term "thienyl" includes the 2-, and 3-isomers and their halogen and lower alkyl substituted analogs; and the term "imidazolyl" includes the 2-, and 4-isomers, and their halogen and lower alkyl substituted analogs. When the moiety "Ar" is the X'—, Y'—, Z'— substituted phenyl radical, it is preferred that the substituents be halogen which may be in the ortho, meta and/or para positions of the phenyl group. In those compounds in which the X substituent is other than hydrogen, it may be at any of the 5-, 6-, 7-, or 8-positions of the imidazo[1,5-a]pyridine nucleus which are not already substituted by the "Z—$B_m$—W" group of Formula I or by the

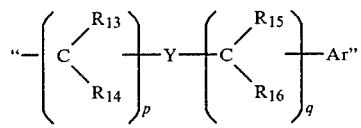

group of Formula II, said latter groups being preferably at the 8-position. When $R_4$ and $R_5$ are other than hydrogen, it is preferred that they be methyl or ethyl. Similarly "B" when employed as part of $ZB_mW$ moiety, is preferably methylene (—$CH_2$—) when z is —O— or —NH—, and ethylene or propenyl when Z represents a single bond.

A preferred subgroup of compounds of Formula I are those wherein $R_2$ and $R_3$ each independently represent hydrogen, loweralkyl with 1 to 3 carbon atoms, —$CH_2OH$, —$CH_2CN$, —$NH_2$, —NO,

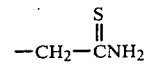

or —$CH_2$—O—CO—$R_1$, wherein $R_1$ represents methyl, ethyl, propyl, isopropyl, t-butyl, dimethylaminomethyl; or —S$(O)_n$—$CH_3$, wherein n is zero, one or two;

X represents hydrogen;

Z represents —O—, —NH—, —S— or a single bond;

B and $B_m$ each represent a branched or straight chain lower alkylene group having up to 5 carbon atoms; and W is allyl or Ar wherein Ar is selected from substituted phenyl, phenyl, thienyl, or pyridyl groups, wherein at least one of the substituents on the phenyl group is independently selected from —H, —Cl, —F, $CH_3$, —t-butyl, —$CF_3$, —$OCH_3$, —CN and —OH.

A more preferred subgroup of compounds of the preferred subgroup of Formula I are those substituted at the 8-position by "Z—$B_m$W" and Ar is phenyl or 3-thienyl.

Preferred compounds of Formula I are represented by the following formula

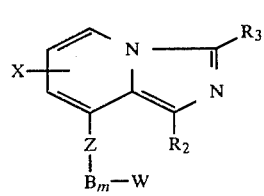

wherein R$_2$ and R$_3$ independently represent H, —CH$_3$, —CH$_2$OH, —CH$_2$CN, —NO or —NH$_2$; X represents hydrogen; Z represents —O—, —NH— or a single bond; B$_m$ represents —CH$_2$—, —CH$_2$—CH$_2$—,

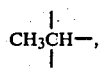

—CH$_2$—CH$_2$—CH$_2$— or —CH=CH—CH$_2$—; and W represents Ar wherein Ar is phenyl, o- or p-fluorophenyl, p-chlorophenyl, 2,4,6-trimethylphenyl, 2-thienyl or 3-thienyl. The most preferred compounds of formula I are those substituted by "Z—B$_m$—W" at the 8-position wherein: R$_2$ and R$_3$ independently represent —H, —CH$_3$, —CH$_2$CN, —NH$_2$, or —CH$_2$OH; X represents hydrogen; Z represents —O—, —NH—, or a single bond; when Z is —O— or —NH—, B$_m$ represents —CH$_2$—, and when Z represents a single bond, B represents —CH$_2$CH$_2$— or —CH=CH—CH$_2$—; and W represents Ar wherein Ar is phenyl or 3-thienyl.

Other preferred compounds having the substituents as defined in Formula I' can be substituted at the 5, 6, 7 or 8 positions by Z—B$_m$—W although those substituted at the 8 position are more preferred.

Thus, the preferred "Z—B$_m$—W" substituents of formula I include phenylmethoxy (also called benzyloxy), benzylamino, thienylmethoxy, thienylmethylamino, phenylethyl, 3-phenylpropenyl, or thienylethyl.

Preferred compounds of formula II include those wherein

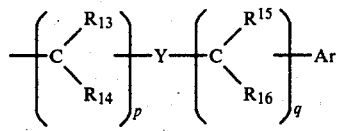

is phenoxymethyl and most preferred are those substituted at the 8-position of the imidazo[1,5-a]pyridine nucleus.

The following compounds are typical representatives of the preferred compounds of this invention:

(1) 1-Methyl-8-(2,4,6-trimethylbenzyloxy)imidazo[1,5-a]pyridine;
(2) 8-(2-Fluorobenzyloxy)-1-methylimidazo[1,5-a]pyridine-3-acetonitrile:
(3) 8-(4-Fluorobenzyloxy)-1-methylimidazo[1,5-a]pyridine-3-acetonitrile:
(4) 1-Methyl-8-(2-phenylethyl)imidazo[1,5-a]pyridine;
(5) 8-(4-Chlorobenzyloxy)-1-methylimidazo[1,5-a]pyridine;
(6) 3-Cyanomethyl-1-methyl-8-(2-thienylmethoxy)imidazo[1,5-a]pyridine;
(7) 8-(4-chlorobenzyloxy)-3-cyanomethyl-1-methylimidazo[1,5-a]pyridine;
(8) 8-(4-Chlorobenzyloxy)-3-hydroxymethyl-1-methylimidazo[1,5-a]pyridine;
(9) 8-Benzyloxy-1-cyanomethylimidazo[1,5-a]pyridine;
(10) 8-Benzyloxy-3-cyanomethylimidazo[1,5-a]pyridine;
(11) Methyl 8-benzyloxy-1-methylimidazo[1,5-a]pyridine-3-acetate;
(12) 8-Benzyloxy-3-cyanomethyl-1-hydroxymethylimidazo[1,5-a]pyridine;
(13) 3-Hydroxymethyl-1-methyl-8-(2-phenylethoxy)imidazo[1,5-a]pyridine;
(14) 8-Benzyloxy-1,3-dimethylimidazo[1,5-a]pyridine;
(15) 3-Cyanomethyl-1-methyl-8-(2-phenylethoxy)imidazo[1,5-a]pyridine;
(16) 3-Cyanomethyl-1-methyl-8-(1-phenylethoxy)imidazo[1,5-a]pyridine;
(17) 3-Cyanomethyl-1-methyl-8-(2-phenylethyl)imidazo[1,5-a]pyridine;
(18) 8-Benzyloxy-1-methylimidazo[1,5-a]pyridine-3-thioacetamide;
(19) 3-Hydroxymethyl-1-methyl-8-(2-phenylethyl)imidazo[1,5-a]pyridine;
(20) 3-Cyanomethyl-1-methyl-8-(3-phenylpropoxy)imidazo[1,5-a]pyridine;
(21) 8-Benzylamino-1,3-dimethylimidazo[1,5-a]pyridine
(22) 8-Benzyloxy-3-cyanomethyl-1-methylimidazo[1,5-a]pyridine;
(23) 8-Benzyloxy-3-hydroxymethyl-1-methylimidazo[1,5-]pyridine;
(24) 3-Hydroxymethyl-8-(2-fluorobenzyloxy)-1-methylimidazo[1,5-a]pyridine;
(25) 3-Cyanomethyl-8-(2-fluorobenzyloxy)-1-methylimidazo[1,5-a]pyridine;
(26) 3-Cyanomethyl-8-(4-fluorobenzyloxy)-1-methylimidazo[1,5-a]pyridine;
(27) 3-Cyanomethyl-1-methyl-8-(2,4,6-trimethylbenzyloxy)imidazo[1,5-a]pyridine;
(28) 8-Benzylamino-3-cyanomethyl-1-methylimidazo[1,5-a]pyridine;
(29) 3-Cyanomethyl-1-methyl-8-(3-thienylmethoxy)imidazo[1,5-a]pyridine;
(30) 1-Methyl-8-phenylmethoxyimidazo[1,5-a]pyridine;
(31) 3-Amino-1-methyl-8-phenylmethoxyimidazo[1,5-a]pyridine and the phosphate addition salt thereof;
(32) 3-Cyanomethyl-1-methyl-8-(3-phenylpropyl)imidazo[1,5-a]pyridine;
(33) 3-Methyl-8-(2-phenethyl)imidazo[1,5-a]pyridine and the hydrochloride salt thereof;
(34) 8-Benzyloxy-3-methylimidazo[1,5-a]pyridine and the hydrochloride salt thereof;
(35) 8-Benxyloxy-1-cyanomethyl-3-methylimidazo[1,5-a]pyridine;

DETAILED DESCRIPTION OF THE INVENTION

There is no single generic preparative method by which the compounds of this invention can be prepared because of the nature and positioning of the various substituents on the imidazo[1,5-a]pyridine nucleus. Generally, the compounds can be prepared by known methods. The particular methods and sequence of reactions is dictated by the specific substituents and their positions and more than one sequence of reactions may be used for certain of the specific compounds of subgenus within the scope of this invention. Generally, the imidazo[1,5-a]pyridine compounds of this invention are prepared by using a substituted pyridine or partially substituted imidazo[1,5-a]pyridine as the starting materials as discussed hereinafter. Some of these intermediates are known compounds. Some are novel, particularly certain substituted aminopyridines such as 3-phenylmethoxy-2-hydroxymethylpyridine, 3-benzyloxy-2-phthalimido-methylpyridine, 2-aminomethyl-3-phenylmethoxypyridine, 2-aminomethyl-3-(2-phenylethyl)pyridine and 2-acetamidomethyl-3-(2-phenylethyl)pyridine. These novel intermediate compounds are represented by the formula

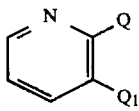

wherein
Q represents hydroxymethyl, phthalimidomethyl, aminomethyl or acetamidomethyl; and
Q1 represents phenylmethoxy or phenylethyl.

The imidazo[1,5-a]pyridine intermediates substituted in e.g. the 8-position are conveniently prepared by reacting a 2-aminomethyl-3-substituted pyridine with a reactive acyl halide followed by cyclization with phosphoryl chloride. The first reaction preferably takes place at about room temperature in an anhydrous solvent which is unreactive toward the acyl halide. The second reaction conveniently takes place at reflux temperatures. A suitable starting compound for the 8-substituted intermediates and final products, e.g. a 2-aminomethyl-3-arylalkoxypyridine, is conveniently prepared by a phase transfer catalyzed alkylation of a 3-hydroxy-2-hydroxyalkylpyridine with an arylalkyl halide in a basic medium at temperatures of about +20° C. to +50° C., followed by conversion of the hydroxymethyl substitutent to a phthalimide derivative by reaction with methanesulfonyl chloride in cold temperatures of about −10° C. to +5° C. then with potassium phthalimide at about room temperature. The phthalimide derivative is then converted to the starting material, 2-aminomethyl-3-arylalkoxypyridine by heating under reflux in the presence of dimethylamine. Pyridines substituted at the 4-, 5- and 6-positions are used to prepare intermediate and final product imidazo[1,5-a]pyridines substituted at the 5-, 6- and 7-positions using analogous processes.

An alkyl group can be introduced at the 1-position of the imidazo[1,5-a]pyridine nucleus by cyclization of an alkyl substituted aminomethyl pyridine as disclosed by Bower et. al., J.Chem. Soc., 2834–37 (1955). For example, preparation of an alkyl-substituted pyridine can be accomplished by the following: the nitrogen of 2-picoline is oxidized by hydrogen peroxide in acetic acid; the resulting compound is converted to a 2-hydroxymethyl-pyridine by treatment with acetic anhydride followed by treatment with ethanolic potassium hydroxide. An alkyl group is introduced on the carbon of the hydroxymethyl group by oxidizing it to the aldehyde, with e.g. manganese dioxide, then introducing the additional alkyl substitutent by reaction with an organometallic reagent such as a Grignard reagent, (R)$_2$CuLi or the like, followed by oxidation to the ketone. Reductive amination under conventional conditions forms the 2-aminoalkyl-substituted methyl-pyridine which then can be cyclized as discussed above.

If it is desired to introduce a substitutent only at the three position, the 2-aminomethyl pyridine is reacted with the appropriate acyl halide then cyclized with phosphoryl chloride as discussed above.

The above reactions, while mainly described to show how alkyl substitutents can be introduced are equally applicable for the introduction of other substitutents by using reactants which are analogously substituted. For example, a cyanomethyl group can be introduced at the three position of the imidazo[1,5-a]pyridines by reacting 2-aminomethyl pyridine with cyanoacetyl chloride. The cyanomethyl group can be introduced at the one position of the imidazo[1,5-a]pyridines by reacting 3-methyl-imidazo[1,5-a]pyridine with dimethylamine hydrochloride and paraformaldehyde, then transforming the resulting compound into a quaternary salt with e.g. methyliodide, and subsequent reaction with sodium cyanide.

A hydroxymethyl group can be introduced at the one position of a 3-substituted-imidazo[1,5-a]pyridine by reaction of the compound with dimethylformamide and phosphoryl chloride to form the aldehyde followed, by reduction. The hydroxymethyl group can be introduced at the three position of a 1-substituted imidazo[1,5-a]pyridine by reaction with phenyllithium and dimethylformamide to form the aldehyde, followed by reduction.

An amino group can be introduced at the one position of an imidazo[1,5-a]pyridine by reacting it with a mixture of nitric acid and sulfuric acid to introduce a nitro substitutent as described by Glover et al, J.Chem.Soc.Perkin Trans. I 957–62 (1980), then reducing the nitro group to an amino group using conventional reaction conditions. An amino substitutent can be introduced at the three position of a 1-substituted imidazo[1,5-a]pyridine by reaction with phenyldiazonium chloride at a basic pH followed by reduction under conventional reaction conditions or via nitration as disclosed by Glover et al. above.

Use of a 2-aminomethyl-3-substituted pyridine in the chemical reactions results in a corresponding substituted imidazo[1,5-a]pyridine. For example, use of a 2-aminomethyl-3-arylalkylpyridine produces an imidazo[1,5-a]pyridine wherein "Z" of formula I is a bond connecting "B—W" of formula I at the 8-position thereof. Other transformations to the compounds of this invention wherein "Z" represents sulfur-, sulfinyl and sulfonyl moieties are also effected via the use of standard methods for introducing these moieties to a pyridine ring, e.g. when sulfur is introduced it can be oxidized to sulfinyl or sulfonyl. Similarly, the preparations of the tetrahydro and perhydro derivatives are effected in accordance with reduction methods which are well known for introducing hydrogen to heterocyclic and aromatic rings.

Means for introducing substitutions at the 8-position in 1-substituted compounds, i.e. those with a 1-lower alkyl, e.g. methyl, can be accomplished as follows: 8-hydroxy-1-methylimidazo[1,5-a]pyridine may be transformed to the desired corresponding 1-methyl-8-phenylalkoxyimidazo[1,5]pyridine by standard alkylation procedures such as heating it with a benzyl halide in the presence of a base, e.g. sodium hydride, and an organic solvent, e.g. dimethylformamide.

Preferably, compounds bearing an acetonitrile substituent at the 3-position can be prepared from a 3-substituted-2-aminomethylpyridine, e.g. 2-aminomethyl-3-arylalkoxypyridine. The reaction is effected by reacting the pyridine with cyanoacetyl chloride to obtain 2-cyanoacetamidomethyl-3-arylalkoxypyridine followed by ring closure with phosphoryl chloride to obtain the desired 8-arylalkoxyimidazo[1,5-a]pyridine-3-acetonitrile.

Alternatively, the desired compounds bearing an acetonitrile substituent at the 3-position can be prepared from an imidazo[1,5-a]pyridine bearing a hydroxymethyl substitutent at the 3-position, e.g. 3-hydroxymethyl-8-phenylmethoxyimidazo[1,5-a]pyridine. In effecting this transformation, the imidazo[1,5-a]pyridine is first reacted with excess phosphoryl chloride to produce the corresponding 3-chloromethyl analog which substitutent is converted to the desired acetonitrile by reaction with an alkali metal cyanide in the presence of an organic solvent, e.g. DMSO or acetonitrile.

Preparation of one of the key intermediates used in the preparation of the desired imidazo[1,5-a]pyridines involves the reaction of an appropriately substituted 2-hydroxymethyl-3-hydroxypyridine with an arylalkyl halide under phase-transfer catalytic conditions to afford a 2-hydroxymethyl-3-arylalkoxypyridine followed by conversion of the hydroxymethyl to an aminomethyl. The phase transfer reaction is generally effected by admixing the reactants at or below room temperature in a mixture of a water-immiscible organic solvent and aqueous hydroxide, preferably 40–50% sodium hydroxide, in the presence of 1 mole percent of a phase-transfer catalyst, preferably methyltrialkyl ($C_8$–$C_{10}$) ammonium chloride, e.g. Adogen 464.

In general, for preparing compounds of formula I wherein Z represents S, O, $NR_6$, or a single bond, the following process (A) may be used

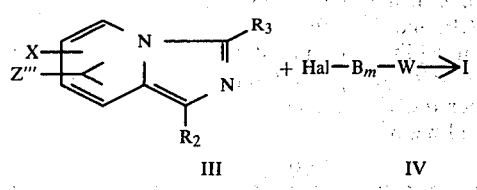

III      IV

In the above Formulas III and IV, Hal represents Br, Cl or I; Z''' represents halogen (Cl, Br, I), OH or SH; W represents phenyl, thienyl, imidazolyl, furanyl or substituted phenyl; and X, $R_2$, $R_3$ and $B_m$ are as defined above.

The reactants are heated together under standard reaction conditions known from the preparation of similar compounds, e.g., in an inert solvent in the presence of a base. When Z''' represents halogen, a copper catalyst is preferably used. When Z''' represents OH or SH, the reaction may be carried out with or without such copper catalyst.

Compounds of the above formula III wherein Z''' is OH, upon reaction with an arylcarbonyl halide, e.g. benzoyl chloride, yields a 5-, 6-, 7- or 8- benzoyloxyimidazo[1,5-a]pyridine of formula II, e.g. wherein p is zero, Y is O and

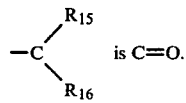

is C=O.

In preparing compounds of Formula II, the substituent

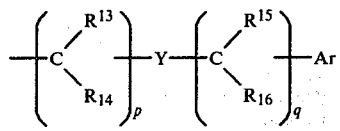

wherein Y is O, S, or $NR_6$, may be introduced by chemical modification of the corresponding imidazo[1,5-a]pyridine having a formyl group at one of positions 5, 6, 7, or 8. Thus, for example, 8-formylimidazo[1,5-a]pyridine having $R_2$ and $R_3$ substitutents as defined hereinabove, upon reduction with sodium borohydride is converted to the corresponding 8-hydroxymethyl derivative, an intermediate for preparing compounds of formula II wherein Y is O or S. Etherification of the 8-hydroxymethyl intermediate, e.g. by treatment with sodium hydride followed by reaction of the resulting sodium salt with an arylalkyl halide, produces an 8-arylalkoxymethyl derivative of formula II. Alternatively, replacement of the hydroxyl group with a leaving group, e.g. tosyl, followed by displacement thereof with an aryloxy alkali metal salt, e.g. sodium phenoxide, produces an 8-aryloxymethyl derivative of formula II.

Similarly, replacement of the hydroxyl group with a good leaving group followed by displacement thereof with an appropriate thio reagent, e.g. an alkali metal salt of an arylalkylthiol or an arylthiol, produces compounds of formula II wherein Y is sulfur; e.g. an 8-arylalkylthiomethyl- or an 8-arylthiomethyl- derivative, respectively.

An imidazo[1,5-a]pyridine having a formyl group at one of positions 5, 6, 7 or 8 is also a useful intermediate in introducing substituents of formula II wherein Y is nitrogen. Thus, for example, reaction of 8-formylimidazo[1,5-a]pyridine having $R_2$ and $R_3$ substituents as defined hereinabove with an arylamine or an aralkylamine followed by reduction of the resulting imines produces 8-arylaminomethyl- and 8-aralkylaminomethyl derivatives of formula II. Treatment of the foregoing secondary amine derivatives with a base followed by reaction with a hydrocarbon halide yields the corresponding tertiary amine derivatives of formula II, i.e. compounds wherein Y is $NR_6$ with $R_6$ being other than hydrogen.

Compounds of this invention having an olefinic functionality at positions 5, 6, 7 or 8, i.e. compounds of formula I wherin Z is a bond and $B_m$ is an $\alpha(\beta)$ or $\beta(\gamma)$-unsaturated lower alkylene, are derived from the corresponding formylimidazo[1,5-a]pyridines having $R_2$ and $R_3$ substituents as defined above, upon reaction thereof under Wittig conditions or modifications thereof.

The starting compounds in the above reaction (A) are either known or may be obtained according to standard procedures.

Compounds of Formula I wherein Z represents SO or $SO_2$ may be obtained by oxidizing the corresponding compound wherein Z represents S, according to procedures well known in the art.

Numerous standard reactions may be applied for transferring one type of substituent $R_2$ and/or $R_3$ into another type. Thus, for example, for preparing compounds of Formula I wherein $R_3$ represents the group BCN, the following processes may be applied.

1. A compound of Formula I wherein $R_2$, X, $B_m$, Z and Ar are as defined for Formula I and $R_3$ represents either $BCONH_2$ or

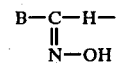

is subjected to dehydration. The reaction is carried out by treating the starting compounds with a suitable dehydrating agent in an inert solvent. Preferred dehydrating agents are $(CF_3CO)_2O$ (in pyridine), $SeO_2$, $POCl_3$, and the like. The starting compounds may be obtained according to standard procedures.

2. A compound of Formula I wherein $R_2$, X, $B_m$, Z and Ar are as defined for formula I and $R_3$ represents the group

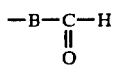

is treated with a suitable reagent, e.g. Tosyl-$CH_2$-NC in the presence of potassium-t-butoxide whereby the formyl function is replaced by $CH_2CN$.

3. A compound of Formula I wherein $R_2$, X, $B_m$, Z and Ar are as defined for Formula I and $R_3$ represents the group —B—COOR is treated with suitable reagent, e.g. dimethylaluminumamide resulting in a compound where $R_3$ is —BCN.

4. A compound of Formula I wherein $R_2$, X, $B_m$, Z and Ar are as defined for Formula I and $R_3$ represents the group

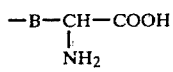

is treated with NaOCl under standard conditions.

5. A compound of Formula I wherein $R_2$, X, $B_m$, Z and Ar are as defined for Formula I and $R_3$ represents a group B—$CH_2NO_2$ is subjected to a reductive dehydration, e.g. with $PCl_3$ and the like in pyridine to give the desired nitrile. [See J. Org. Chem. 42, 3956 (1977)].

6. A compound of Formula I wherein $R_2$, X, $B_m$, Z and Ar are as defined for Formula I and $R_3$ represents H is reacted with a compound of the formula Hal—B—CN wherein Hal is chlorine or bromine, in the presence of a Lewis acid, e.g. aluminum chloride, zinc chloride, boron chloride and the like, or a phase transfer catalyst.

7. A compound of Formula I wherein $R_2$, X, $B_m$, Z and Ar are as defined for Formula I and $R_3$ represents the group

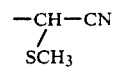

is subjected to a reduction, preferably with Raney-nickel whereby the —$SCH_3$ group is replaced by a hydrogen atom. The starting compound may be obtained by reacting a compound of Formula I wherein $R_3$ represents hydrogen with $CH_3$—S—CH(Cl)CN by means of a Friedel Crafts catalyst, e.g. $SnCl_4$, $TiCl_4$, $AlCl_3$, and the like.

In addition to modifying various $R_3$ groups into —B—CN groups as described in the above reactions, other transformations may be carried out, e.g. as indicated below:

TABLE I

| STARTING $R_3$ | CHEMICAL REACTION | RESULTING $R_3$ |
| --- | --- | --- |
| —$BCOOC_2H_5$ | reduction ($LiAlH_4$) | —$BCH_2OH$ |
| —$CH_2CN$ | reaction with alkylhalide, base | $\begin{array}{c}\text{alkyl}\\\|\\-CH-CN\end{array}$ |
| —BCN | reduction with $LiAlH_4$ | —$BCH_2NH_2$ |
| —$BCH_2NH_2$ | 1. reaction with methyliodide 2. followed by reaction with metal cyanide | —$BCH_2CN$ |
| —BCN | saponification | —BCOOH |
| —BOH | reaction with NaH and $ClCON(CH_3)_2$ | —B—$OCON(CH_3)_2$ |
| —BCN | treatment with NaOH | —$BCONH_2$ |
| —BCN | treatment with $H_2S$ | —B—$CSNH_2$ |
| —BOH | treatment with $SOCl_2$ | —BCl |
| —BX″ (X″ = leaving group, e.g. halogen) | treatment with $NO_2^\ominus$ | —$BNO_2$ |
| —BX″ X″ = leaving group, e.g. halogen | reaction with $CH_3NO_2$, base | —$BCH_2NO_2$ |
| —CHO | 1. reaction with base, $CH_3NO_2$ resulting in CH=$CHNO_2$ 2. treatment with $NaBH_4$ | $CH_2CH_2NO_2$ |
| $\begin{array}{c}\text{NHAc}\\\|\\-CH_2CH-COOH\end{array}$ | basic hydrolysis | $\begin{array}{c}NH_2\\\|\\-CH_2CH-COOH\end{array}$ |
| H | nitration ($HNO_3$/Acetic Acid) | —$NO_2$ |
| H | nitrosation | —NO |
| $\begin{array}{c}O\\\|\|\\-N-(O)_m\end{array}$ (n = 0, 1) | reduction | —$NH_2$ |
| —$NH_2$ | 1. diazotization 2. followed by reaction with an alkali metal | —SCN |

TABLE I-continued

| STARTING R₃ | CHEMICAL REACTION | RESULTING R₃ |
|---|---|---|
| H | thiocyanate halogenation | —Cl<br>—Br |
| H | acylation via acid chloride or acid anhydride | —COC=CH₂<br>—COC≡CH<br>—COCOOR<br>(R = H, alkyl) |
| —COCOOR<br>(R = H, alkyl) | reduction (NaBH₄) | —CHOHCOOR |
| —COR<br>(R = H, alkyl) | treatment with hydrogen cyanide | $\begin{array}{c}\text{OH}\\|\\-\text{C}-\text{CN}\\|\\\text{R}\end{array}$ |
| $\begin{array}{c}\text{OH}\\|\\-\text{C}-\text{CN}\\|\\\text{R}\end{array}$ | esterification | $\begin{array}{c}\text{OCOR}^1\\|\\-\text{C}-\text{CN}\\|\\\text{R}\end{array}$<br>R¹ = hydrocarbon |
| $\begin{array}{c}\text{OH}\\|\\-\text{C}-\text{CN}\\|\\\text{R}\end{array}$ | etherification | $\begin{array}{c}\text{OR}^1\\|\\-\text{C}-\text{CN}\\|\\\text{R}\end{array}$ |
| —CH₂OH | 1. (a) Phosphorylation<br>   (b) or sulfonylation<br>2. followed by esterification or treatment with an alkali metal base | (a) —CH₂—OP(=O)(OR)—OR<br>R = H, alkali metal or alkyl<br>(b) —CH₂—OS(=O)₂—OR |
| —CH₂OH | alkylation with NaH and ClCH₂SCH₃ | —CH₂OCH₂SCH₃ |
| —CH₂OH | alkylation with NaH and ClCH₂SC₆H₅/NaI | —CH₂OCH₂SC₆H₅ |
| —CH₂OH | alkylation with NaH and R—C(=O)—XCH₂Cl/NaI<br>X = O, S, NR; R = H, CH₃ | —CH₂OCH₂XCOR |

Equally the various possibilities of R₂ may, where appropriate, be transferred into other R₂-substituents by reactions such as those outlined for R₃ in the processes described above. Also, the following are other transformations which may be carried out at the one position to modify the R₂ function; which transformations may also be carried out, where appropriate, to modify the R₃ function at the three-position.

TABLE II

| STARTING R₂ | CHEMICAL REACTION | RESULTING R₂ |
|---|---|---|
| $\begin{array}{c}\text{CH}_3\\|\\-\text{CH}-\text{COOC}_2\text{H}_5\end{array}$ | alkylation with NaH and CH₃I | $\begin{array}{c}-\text{C}-(\text{CH}_3)_2\\|\\\text{COOC}_2\text{H}_5\end{array}$ |
| —(CH₂)ₙCOOR<br>R = H, alkyl<br>n = 0, 1 | Reduction | —(CH₂)ₙCHO |
| —(CH₂)ₙCOOH | organometallic reagent (e.g. alkyl lithium) | —(CH₂)ₙ—C(=O)—R<br>(R = alkyl) |
| —(CH₂)ₙCHO<br>(n = 0, 1) | Wittig process | —(CH₂)ₙCH=CH₂ |
| —(CH₂)ₙ—COR<br>(n = 0, 1; R = alkyl) | Wittig process | —(CH₂)ₙCR=CH₂ |
| —(CH₂)ₙCH=CH₂<br>(n = 0, 1) | halogen addition and elimination | —(CH₂)ₙCR≡CH |
| $\begin{array}{c}\text{R}\\|\\-\text{CHOH}\end{array}$<br>(R = H, alkyl) | 1. replacement of OH with leaving group (e.g. tosyl)<br>2. nucleophilic displacement with LiC≡CH | —CHRC≡CH |
| —CHR—C≡CH<br>(R = H, alkyl) | isomerization (acid or base) | $\begin{array}{c}\text{R}\\|\\-\text{C}=\text{C}=\text{CH}_2\end{array}$ |
| —OH<br>—OH<br>—SH | reaction with P₂S₅<br>etherification<br>etherification | —SH<br>—OR<br>—SR<br>(R = alkyl) |
| —NHCOOR<br>(R = H, alkyl) | hydrolysis | —NH₂ |

The sequence of certain reactions may be altered, thus, for example, one may, in accordance with methods described herein, first prepare a compound of the formula III shown hereinabove, make the above described rearrangements within the groups $R_2$ and $R_3$ and then complete the molecule by carrying out process (A) described above.

The term "pharmaceutically acceptable salts" of this invention include salts wherein the acidic hydrogen in the carboxylic acid derivatives of this invention (e.g. wherein $R_2$=COOH) is replaced with a cation (e.g. sodium) as well as salts wherein an acidic hydrogen forms an acid addition salt with an amine, e.g. the phosphate salt of 3-amino-1-methyl-8-phenylmethoxyimidazo[1,5-a]pyridine.

Among the pharmaceutically acceptable cationic salts contemplated for this invention are salts of alkali and alkaline earth metals, e.g. sodium, potassium, and calcium, also aluminum, as well as salts with an amine, such as an N-methyl glucamine salt.

Suitable acids for the pharmaceutically acceptable acid addition salts include hydrochloric, sulfuric, phosphoric, nitric, acetic, propionic, maleic, ascorbic, citric and the like.

Both the cationic salts and acid addition salts are prepared via procedures well known in the art.

The following examples illustrate the preparation of compounds and compositions of this invention. All temperatures are in degrees Celsius.

EXAMPLE 1

Add 68 ml of triethylamine with stirring to a solution of 75 gm 3-phenylmethoxy-2-hydroxymethyl pyridine (prepared by phase transfer-catalyzed alkylation of 3-hydroxy-2-hydroxymethyl pyridine with benzyl chloride) in 750 ml dichloromethane at −5°. Also add a solution of 29.6 ml methanesulfonyl chloride in 200 ml dichloromethane over a period of 0.75 hours at −5°. Then stir the reaction mixture an additional hour at −5°.

Filter off the triethylamine hydrochloride which forms and wash the filtrate successively with cold water, cold 2% sodium bicarbonate solution and brine. Concentrate under reduced pressure the resulting dichloromethane solution to a volume of approximately 200 ml., then add 800 ml dimethylformamide. Add 65 gm potassium phthalimide to the resulting solution and stir for 18 hours at room temperature. Pour the reaction mixture into 8 liters of ice/water and stir for 0.5 hours. Isolate the resulting solid by filtration, wash thoroughly with cold water and dry in vacuo to yield the phthalimide derivative, 3-benzyloxy-2-phthalmidomethylpyridine, mp 179°–180°.

EXAMPLE 2

Heat 75 gm of 3-benzyloxy-2-phthalimidomethylpyridine under reflux for one hour in 550 ml of a 40% aqueous dimethylamine solution. Cool the resulting reaction mixture to room temperature, then dilute it with 550 ml water and extract with dichloromethane. Wash the dichloromethane extract with brine and dry over anhydrous sodium sulfate. Filter the dried reaction mixture and remove the solvent dichloromethane from the filtrate under reduced pressure, yielding 2-aminomethyl-3-phenylmethoxypyridine, BP 145°–155°/0.5 mm.

EXAMPLE 3

Add dropwise with stirring a solution of 3.5 ml acetyl chloride in 50 ml THF (tetrahydrofuran) to a cooled solution of 10 gm of 2-aminomethyl-3-phenylmethoxypyridine and 7.1 ml triethylamine in 125 ml THF. Warm to room temperature and stir an additional hour. Remove triethylamine hydrochloride by filtration and evaporate the filtrate under reduced pressure. Recrystallize the residue from toluene to obtain 2-acetamidomethyl-3-(phenylmethoxy)pyridine, mp 94°–96°.

EXAMPLE 4

Heat under reflux for 0.5 hours a mixture of 5 gms of the compound produced in Example 3 and 75 ml phosphorous oxychloride. Cool the reaction mixture to room temperature and remove the phosphorous oxychloride under reduced pressure. Partition the residue between chloroform and an aqueous solution of sodium bicarbonate. Separate the chloroform layer and dry over potassium carbonate. Filter the resulting dry solution and remove the chloroform from the filtrate under reduced pressure. Chromatograph the residue on silica gel using ethyl acetate-chloroform. Combine the fractions containing the desired product, 3-methyl-8-(phenylmethoxy)imidazo[1,5-a]pyridine and remove the solvent under reduced pressure. Dissolve the resulting solid in absolute ethanol and add an ethanolic hydrogen chloride solution. Remove the ethanol under reduced pressure and recrystallize the residue from acetonitrile to obtain 3-methyl-8-(phenylmethoxy)imidazo[1,5-a]pyridine hydrochloride, mp 174°–175°.

EXAMPLE 5

Heat under reflux for 2 hours a mixture containing 3.1 gm 3-methyl-8-(phenylmethoxy)imidazo[1,5-a]pyridine, 1.25 gm dimethylamine hydrochloride and 0.54 gm paraformaldehyde in 50 ml ethanol. Cool the reaction mixture to room temperature and remove the ethanol under reduced pressure and partition the residue between chloroform and saturated sodium bicarbonate. Extract the aqueous layer with chloroform and combine the chloroform extracts. Dry the combined extracts over anhydrous potassium carbonate and filter. Remove the chloroform from the filtrate under reduced pressure and chromatograph the residue on silica gel using chloroform and tetrahydrofuran. Combine the fractions containing the desired product, 1-dimethylaminomethyl-3-methyl-8-(phenylmethoxy)imidazo[1,5-a]pyridine, and remove the solvent under pressure to obtain the desired product as a solid.

EXAMPLE 6

Dissolve the product produced in Example 5 in 120 ml acetone, then add 1.3 gm methyl iodide and stir the reaction mixture for 12 hours at room temperature. Remove the acetone under reduced pressure and dissolve the resulting residue in 40 ml dimethylformamide. Add 0.86 gms finely powdered sodium cyanide and heat the reaction mixture on a steam bath for 1 hour. Cool to room temperature and remove the dimethylformamide in vacuo. Partition the residue between chloroform and water and extract the aqueous layer with chloroform. Combine the chloroform extracts and dry them over anhydrous potassium carbonate. Filter the dry solution and remove the chloroform under reduced pressure. Recrystallize the residue from ethyl acetate to obtain 1-cyanomethyl-3-methyl-8-(phenylmethoxy)imidazo[1,5-a]pyridine, mp 118°–119°.

EXAMPLE 7

Add dropwise with stirring at 0° a solution of 162 ml borane-methylsulfide, 2 M, in THF to a solution of 20 gms 3-(2-phenylethyl)picolinamide in 500 ml THF. Then heat the reaction mixture under reflux for 8 hours. Cool to room temperature and remove the THF under reduced pressure. Dissolve the residue in 125 ml ethanol and 125 ml 12 N hydrochloric acid. Heat the solution under reflux for 2 hours then cool to room temperature. Remove the ethanol under reduced pressure and basify the aqueous layer with 40% sodium hydroxide. Extract the aqueous layer with chloroform. Combine the extracts and dry the combined extracts over anhydrous potassium carbonate. Filter the resulting dry solution and remove the chloroform from the filtrate under reduced pressure. Chromatograph the residue on silica gel using ethyl acetate, dichloromethane and THF. Combine the fractions containing the desired product, 2-aminomethyl-3-(2-phenylethyl)pyridine, and remove the solvent under reduced pressure to obtain the desired product.

EXAMPLE 8

Add dropwise with stirring a solution of 1.24 gm acetyl chloride in 10 ml THF to a cooled solution of 3.2 gm of 2-aminomethyl-3-(2-phenylethyl)pyridine and 2.3 ml triethylamine in 100 ml THF. Warm the reaction mixture to room temperature and then stir for an additional 0.5 hour. Filter off the triethylamine hydrochloride and evaporate the filtrate under reduced pressure. Chromatograph on silica gel using 40% THF in chloroform to obtain 2-acetamidomethyl-3-(2-phenylethyl)pyridine.

EXAMPLE 9

Heat a solution of 3.1 gm of the product of Example 8 and 40 ml phosphorous oxychloride at 100° for 20 minutes. Cool to room temperature and remove the phosphorous oxychloride under reduced pressure. Partition the residue between chloroform and an aqueous solution of sodium bicarbonate. Separate the chloroform layer, wash it with brine and dry over potassium carbonate. Filter the dry solution and remove the chloroform under reduced pressure. Dissolve the residue in absolute ethanol and add an ethanolic solution of hydrogen chloride. Remove the ethanol under reduced pressure. Triturate the resulting residue in ether to obtain 3-methyl-8-(2-phenylethyl)imidazo[1,5-a]pyridine hydrochloride hemihydrate as an amorphous, hygroscopic solid.

By following the appropriate process of those disclosed and exemplified above, and using the appropriately substituted starting materials, it is possible to prepare all further compounds falling within the scope of this invention, including those shown in the following Tables III and IV.

TABLE III

| | X-hydrogen unless otherwise noted. | |
|---|---|---|
| $R_2$ | $R_3$ | $Z-B_m-W$ |
| —$CH_3$ | —$CH_2$—O—CO—$CH_3$ | 8-benzyloxy |
| —CO—O—$C_2H_5$ | —$CH_2$—N($CH_3$)$_2$ | 8-benzyloxy |
| —$CH_3$ | —$CH_2$—N($CH_3$)$_2$ | 8-(2-pyridylmethoxy) |
| —$CH_3$ | —CH(OH)—$CH_3$ | 8-benzyloxy |
| —$CH_3$ | —$CH_2OH$ | 8-(3,4-dichlorobenzyloxy) |
| —$CH_3$ | —$CH_2OH$ | 8-(4-t-butylbenzyloxy) |
| —$CH_3$ | —$CH_2OH$ | 8-(3-trifluoromethylbenzyloxy) |
| —$CH_3$ | —C($CH_3$)$_2$—CN | benzyloxy |
| —$CH_3$ | —$CH_2$—O—CO—C($CH_3$)$_3$ | benzyloxy |
| —$CH_3$ | H | benzylthio |
| H | —$CH_2CN$ | 8-benzyloxy |
| —$CH_3$ | —$CH_2CN$ | 8-(4-chlorobenzyloxy) |
| —$CH_3$ | H | 8-(2-phenylethoxy) |
| —$CH_3$ | —$CH_3$ | 8-benzyloxy |
| —$CH_3$ | H | 8-(2-phenylethyl) |
| —$CH_3$ | —$CH_2$—N($CH_3$)$_2$ | 8-benzylthio |
| —$CH_3$ | —CH($CH_3$)—CN | 8-benzyloxy |
| —$CH_3$ | —$CH_2CN$ | 8-(4-t-butylbenzyloxy) |
| —C($CH_3$)$_3$ | H | 8-benzyloxy |
| —$CH_3$ | —$CH_2$—N($CH_3$)$_2$ | 8-(4-trifluoromethylbenzyloxy) |
| —$CH_3$ | H | 8-(4-t-butylbenzyloxy) |
| —$CH_3$ | —$CH_2CN$ | 3-(1-phenylethoxy) |
| —$CH_3$ | —$CH_2CN$ | 8-phenylethyl |
| —$CH_3$ | —$CH_2CN$ | 8-benzyloxy [X = 5-$CH_3$] |
| —$CH_3$ | H | 8-(2,4,6-trimethylbenzyloxy) |
| —$CH_3$ | —$CH_2N(CH_3)_2$ | 8-(2,4,6-trimethylbenzyloxy) |
| —$CH_3$ | $CH_2OH$ | 8-phenylethyl |
| —$CH_3$ | —$CH_2CN$ | 8-(2,4,6-trimethylbenzyloxy) |
| —$CH_3$ | —$CH_2CH_3$ | 8-benzyloxy |
| —$CH_2$—O—CO—C($CH_3$)$_3$ | —$CH_2CN$ | 8-benzyloxy |
| —$CH_2OH$ | H | 8-benzyloxy |

TABLE III-continued

| | X-hydrogen unless otherwise noted. | |
|---|---|---|
| R₂ | R₃ | Z—B$_m$—W |
| —CH₃ | H | 8-(2-pyridylmethoxy) |
| —CH₃ | —CH₂CN | 8-(2-pyridylmethoxy) |
| —CH(CH₃)₂ | H | 8-benzyloxy |
| —CH₃ | —CH₂CN | 8-(4-methylsulfonyl-benzyloxy) |
| —CH₃ | —CH₂CN | 8-(benzyloxy [X = 6-Cl] |
| —CH₂—CH₃ | H | 8-benzyloxy |
| —CH₂—CH₃ | —CH₂CN | 8-benzyloxy |
| 2-pyridyl | H | 8-benzyloxy |
| phenyl | H | 8-benzyloxy |
| p-methylsulfonyl-phenyl | H | 8-benzyloxy |
| p-methylsulfonyl-phenyl | —CH₂CN | 8-benzyloxy |
| —CH₂Br | H | 8-benzyloxy |
| —CH₃ | —CH₂—N(CH₃)₂ | 8-(4-cyanobenzyloxy) |
| —CH₃ | H | 8-(4-cyanobenzyloxy) |
| —CH₃ | CH₂CN | 8-(4-cyanobenzyloxy) |
| —CH₃ | —CH₂—CS—NH₂ | 8-benzyloxy |
| —CH₃ | —CH₂—CO—NH₂ | 8-benzyloxy |
| —CH₃ | —CH₂—O—C₂H₅ | 8-benzyloxy |
| —CH₃ | —CH(CH₃)—O—CH₃ | 8-benzyloxy |
| —CH₃ | —CH₂—CO—N(CH₃)₂ | 8-benzyloxy |
| —CH₃ | —CH₂—O—CH₃ | 8-benzyloxy |
| —CH₃ | phenoxymethyl | 8-benzyloxy |
| —CH₃ | —CH₂CS—N(CH₃)₂ | 8-benzyloxy |
| —CH₃ | —CH₂—CN | 8-(phenylpropyloxy) |
| —CH₃ | —CH₃ | 8-benzylamino |
| —CH₃ | —CH₂CN | 8-(3-thienylmethoxy) |
| —CH₃ | —CH₂CN | 8-(4-pyridylmethoxy) |
| —CH₃ | —NHCOCH₃ | 8-benzyloxy |
| —CH₃ | —CH₂CONHCH₃ | 8-benzyloxy |
| —CH₂NH₂ | —CH₃ | 8-benzyloxy |
| —CH₂CN | —CH₂CN | 8-benzyloxy |
| —CH₂—N(CH₃)₂ | —CH₃ | 8-benzyloxy |
| —CH₃ | Br | 8-benzyloxy |
| —CH₃ | —C≡C—CH₃ | 8-benzyloxy |
| —CH₃ | —CH≡CH₂ | 8-benzyloxy |
| —C₂H₅ | —CH₃ | 8-benzyloxy |
| —CH₃ | —CH₂C(=S)—N(morpholino) | 8-benzyloxy |
| —CH₃ | Cl | 8-benzyloxy |
| —COOCH₃ | —CH₃ | 8-benzyloxy |
| —CH₃ | —COCF₂ | 8-benzyloxy |
| —CH₃ | —CHO | 8-benzyloxy |
| —OCH₂CN | H | 8-benzyloxy |
| —CH₃ | —CH(OH)C≡CH | 8-benzyloxy |
| —CH₃ | —CH₂Cl | 8-benzyloxy |
| —CH₂OCH₃ | —CH₃ | 8-benzyloxy |
| —CH₂—N(phthalimido) | —CH₃ | 8-benzyloxy |
| —CF₃ | —CH₂CN | 8-benzyloxy |
| —CH₃ | —CH₂C(=S)—NHCH₃ | 8-benzyloxy |
| —CH₃ | —CH₂CH₂NH₂ | 8-benzyloxy |
| —CH₃ | —CH₂COOC₆H₅ | 8-benzyloxy |
| —CH₂CN | —CH₃ | 8-benzyloxy |
| —CH₂Cl | —CH₃ | 8-benzyloxy |
| —CH₃ | —CH₂CONH₂ | 6-(2-phenylethyl) |
| —CH₃ | —CH₂CONH₂ | 8-(2-phenylethyl) |
| —CH₃ | —CH₂CN | 8-(N—methyl-N—benzyl)amino] |
| —CH₃ | H | 8-benzylaminomethyl |
| —CH₃ | —CH₂N(CH₃)₂ | 8-benzylaminomethyl |

TABLE III-continued

X-hydrogen unless otherwise noted.

| $R_2$ | $R_3$ | $Z-B_m-W$ |
|---|---|---|
| —$CH_3$ | —$CH_2CN$ | 8-(2-furanyl)methylamino |
| —$CH_3$ | —$CH_2CN$ | 8-(3-furanyl)methoxy |
| —$CH_3$ | —$CH_2C(=S)-NH_2$ | 8-(3-thienyl)methoxy |
| —$CH_3$ | —$CH_2CN$ | 8-(1-hydroxy-3-phenyl-propyl) |
| —$CH_3$ | —$CH_3$ | 8-(1-hydroxy-3-phenyl-propyl) |
| —$CH_3$ | —$CH_2CN$ | 8-benzylthio |
| —$CH_3$ | —$CH_2CN$ | 8-(4-toluenesulfonyloxy) |
| —$CH_3$ | —$CH_2N(CH_3)_2$ | 8-(1-hydroxy-3-phenyl-propyl) |
| —$CH_3$ | —H | 8-[1-(3-phenylpropenyl)] |
| —H | —$NH_2$ | 8-[1-(3-phenylpropenyl)] |
| —H | —NO | 8-[1-(3-phenylpropenyl)] |
| —$NH_2$ | —$CH_3$ | 8-[1-(3-phenylpropenyl)] |

TABLE IV $$\left( \underset{R_{14}}{\overset{R_{13}}{\diagup}} C \diagdown \right)_p - Y - \left( \underset{R_{16}}{\overset{R_{15}}{\diagup}} C \diagdown \right)_q - Ar$$

X = Hydrogen unless otherwise noted

| $R_2$ | $R_3$ | |
|---|---|---|
| —$CH_3$ | H | 8-benzyloxymethyl |
| —$CH_3$ | —$CH_2CN$ | 8-benzyloxymethyl |
| —$CH_3$ | —$CH_2CN$ | 8-(4-chlorobenzoyloxy) |
| —$CH_3$ | —$CH_2CN$ | 8-(4-methoxybenzoyloxy) |
| —$CH_3$ | —$CH_2CN$ | 8-(2,4,6-trimethoxy-benzoyloxy) |
| —$CH_3$ | —$CH_2N(CH_3)_2$ | 8-benzyloxymethyl |
| —$CH_3$ | H | 8-(N—acetyl)benzylamino-methyl |
| —$CH_3$ | —$CH_2CN$ | 8-(N—acetyl)benzylamino-methyl |
| —$CH_3$ | —$CH_2CN$ | 8-(N—benzyl)carbamoyl |

The respective X substituted analogues of the X-unsubstituted compounds in the above Tables may also be obtained by the above processes by using the appropriate X-substituted starting compounds.

The compounds of this invention, Formulas I and II, are useful in the treatment of peptic ulcers, have characteristics which enable them to relieve the symptoms of peptic ulcer disease (including stress ulceration) and promote healing of gastric and/or duodenal ulcers. The anti-ulcer activity of the compounds of Formulas I and II is identified by tests which measure their gastric antisecretory activity in the rat and by tests which measure their cytoprotective effect (sometimes also referred to in the art as mucoprotective effect) in rats. The compounds are useful as conjunctive therapeutic agents for coadministration with such anti-inflammatory/analgesic agents as aspirin, indomethacin, phenylbutazones, ibuprofen, naproxen, tolmetin and other agents having the untoward side effect of contributing to damage to the gastrointestinal tract.

The compounds of this invention, in order to be evaluated for their applied use characteristics undergo testing according to standard biological procedures wherein the compounds are evaluated both on an absolute basis and on a comparative basis with compounds known to possess the characteristics useful for the treatment and/or prevention of peptic ulcer disease, duodenal ulcer disease and drug-induced gastric ulceration. Such tests include testing for inhibition of gastric secretion in rats with pyloric ligation techniques and anti-ulcer studies employing aspirin, indomethacin or other agents known to induce gastrointestinal damage. The test compounds are administered in appropriate and well-defined and well-known vehicles for either intraperitoneal delivery or oral administration.

From these and other tests, including cytoprotective tests in rats in which ethanol is employed to induce gastrointestinal damage, the compounds of this invention are found to be effective for the oral treatment of the ulcerative disease states herein mentioned at doses of about 0.5 to 50 mgm per kilogram of body weight per day, preferably being administered in 2–4 divided doses per day. In those instances wherein it is desired to administer the compounds of this invention via a parenteral route, e.g. intravenously, the compounds are administered at a dose range of about 0.01 to 10 mg/kg in single or multiple daily doses. Of course, the dose will be regulated by the attending clinician depending on factors such as the degree and severity of the disease state and age and general condition of the patient being treated. The recommended dose range for the preferred compounds of this invention is an oral dose of 75 to 1600 mg/day, preferably 600 to 800 mg/day, in two to four divided doses to achieve relief of the symptoms of peptic ulcer disease and promote the healing of gastric and/or duodenal ulcers.

In their use in the treatment of peptic ulcer disease, including gastric and duodenal ulcers, and in the prevention and treatment of drug-induced gastric ulceration, the compounds are administered in unit dosage forms such as tablets, capsules, pills, powders, granules, sterile parenteral solutions or suspensions, suppositories and the like. Such preparations are prepared according to standard techniques well known in the art. A few examples of such pharmaceutical formulations follow.

Formulations

The following formulations exemplify some of the dosage forms in which the anti-ulcer agents of this invention may be employed. In each, the active ingredient is designated by the term "Drug" which is meant to indicate one of the following compounds:

3-methyl-8-(phenylmethoxy)imidazo[1,5-a]pyridine as the hydrochloride salt;

3-methyl-8-(phenylmethoxy)imidazo[1,5-a]pyridine-1-acetonitrile; and 3-methyl-8-(2-phenylethyl)imidazo[1,5-a]pyridine as the hydrochloride salt;

It is contemplated, however, that each of these exemplary compounds may be replaced by equally effective quantities of other compounds within the scope of Formulas I and II, particularly those of Formula I; and their pharmaceutically acceptable salts.

Formulation 1

| | Tablets | | |
|---|---|---|---|
| No. | Ingredient | mg/tab | mg/tab |
| 1 | Drug | 25.0 | 400.0 |
| 2 | Lactose impalpable powder USP | 114.0 | 241.5 |
| 3 | Corn starch USP | 25.0 | 50.0 |
| 4 | Corn starch as 5% paste in distilled water | 10.0 | 35.0 |
| 5 | Corn starch USP | 25.0 | 50.0 |
| 6 | Magnesium stearate USP | 1.0 | 3.5 |
| | | 200.0 | 780.0 |

Method of Manufacture

Mix item Nos. 1, 2 and 3 in a suitable blender for 5 to 15 minutes. Pass through a fine screen (#40) if necessary. Reblend for 5 to 10 minutes and granulate with item No. 4. Pass the damp granulated mass through a coarse sieve (#6) using a suitable mill. Dry the damp granules at 40° to 50° C. overnight. Mill the dried granules using No. 20 screen. Add item No. 5 and blend for 5 to 10 minutes. Add item No. 6 and blend further for 3 to 5 minutes. Compress the tablet mixture into an appropriate size and weight tablets using a suitable tabletting machine.

Formulation 2

| | Capsules | | |
|---|---|---|---|
| No. | Ingredient | mg/tab | mg/tab |
| 1 | Drug | 25.0 | 400.0 |
| 2 | Lactose, impalpable powder USP | 144.0 | 191.5 |
| 3 | Corn starch USP | 30.0 | 105.0 |
| 4 | Magnesium stearate USP | 1.0 | 3.5 |
| | | 200.0 | 700.0 |

Method of Manufacture

Mix item Nos. 1, 2 and 3 in a suitable blender for 5 to 10 minutes. Pass through a fine screen (#40) if necessary. Reblend for 5 to 10 minutes, add item No. 4 and mix further for 3 to 50 minutes. Using a suitable machine, encapsulate the mixture into a two-piece hard gelatin capsule of appropriate size.

Formulation 3

| | Suspensions | |
|---|---|---|
| Ingredients | Formula A (mg/ml) | Formula B (mg/ml) |
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |

-continued

| | Suspensions | |
|---|---|---|
| Ingredients | Formula A (mg/ml) | Formula B (mg/ml) |
| Vanillin | 0.2 | 0.2 |
| Purified Water q.s. | 1.0 ml | 1.0 ml |

Method of Manufacture

1. Charge approximately 40% of the final volume of purified water in a stainless steel tank. Heat to boiling. Agitate using an appropriate stirrer. Agitation should continue throughout procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.
7. This suspension is then q.s. to final volume with purified water at 25° C.

Formulation 4

| Parenteral | |
|---|---|
| | mg/ml |
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

Method for Manufacture

1. Dissolve parabens in a portion (approximately 85% of the final volume) of the water for injection at 65°–70° C.
2. Cool to 25°–35° C. Charge and dissolve sodium bisulfite, disodium edetate and sodium sulfate.
3. Charge and dissolve the Drug.
4. Bring the solution to the final volume by adding water for injection.
5. Filter the solution through 0.22μ membrane and fill into appropriate containers.
6. Terminally sterilize the units by autoclaving.

Formulation 5

| Injectable Suspension | |
|---|---|
| | mg/ml |
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

Method of Preparation

1. Dissolve parabens in a portion of water for injection at 65°–70° C.

2. Cool to 25°–35° C. Charge and dissolve benzyl alcohol, sodium citrate, disodium edetate, PEG 4000, povidone and sodium carboxymethylcellulose.
3. Filter the solution and sterilize by autoclaving
4. Make a slurry of the sterile Drug and pass it through a colloid mill.
5. Mix it well with solution from Step 3 and pass it through the mill.
6. Bring the suspension to the final volume/weight and fill into sterile containers.

Formulation 6

| Suppositories | |
|---|---|
| A. Formula | mg/supp |
| Drug | 5.0 |
| Cocoa butter | 1995.0 |
| | 2.0 g. |

Procedure

1. Melt cocoa butter to about 32°–35° C.
2. Blend Drug into cocoa butter until well dispersed.
3. Pour into teflon-coated mold and congeal in refrigerator. Keep in refrigerator for an appropriate length of time.
4. Remove suppositories from mold.

| B. Formula | mg/supp |
|---|---|
| Drug | 100.0 |
| PEG 1000 | 1824.0 |
| PEG 4000 | 76.0 |
| | 2.0 g. |

Procedure

1. Melt PEG 1000 and PEG 4000 in one container to 50° C.
2. Add Drug to the mixture. Blend until well dispersed.
3. Pour into mold and congeal in refrigerator. Keep in refrigerator for an appropriate length of time.
4. Remove suppositories from mold.

Since all the compounds within the large class of compounds encompassed by this invention are not equally therapeutically potent, certain subgroups and certain specific compounds have been found to be preferred for their therapeutic utility. Preferred are those compounds having the imidazo[1,5-a]pyridine nucleus containing an oxygen or nitrogen atom at the 8-position of the imidazo[1,5-a]pyridine nucleus. Another preferred group is where "Ar" represents phenyl or 3-thienyl substituted derivatives thereof. Another preferred group contains the "Ar" moiety attached to the 8-position of the imidazo[1,5-a]nucleus through a methoxy, ethoxy methylamino or ethylamino linkage, i.e., wherein $B_m$ represents methylene or ethylene, and those attached through an ethylene or propenyl linkage, i.e. where Z is a bond and $B_m$ is ethylene or propenyl. Another preferred group are those compounds containing a cyanomethyl, an amino or an alkyl substituent, particularly methyl, at the 1-position or the 3-position. Another preferred group are those compounds having a hydroxyalkyl, preferably hydroxymethyl, at the 1-position or the 3-position. Preferred specific compounds include those imidazo[1,5-a]pyridines of formulas I and II having the following substituents:

| $R_2$ | $R_3$ | X | Z | B | (m) | AR |
|---|---|---|---|---|---|---|
| CH₃ | CH₂CN | H | O | CH₂ | 1 | phenyl |
| CH₂OH | CH₂CN | H | O | CH₂ | 1 | phenyl |
| CH₃ | CH₂CN | H | O | CH₂ | 1 | thienyl |
| CH₃ | NH₂ | H | O | CH₂ | 1 | phenyl |
| CH₃ | CH₂OH | H | O | CH₂ | 1 | phenyl |
| CH₃ | CH₂CN | H | NH | CH₂ | 1 | phenyl |
| CH₃ | CH₂CN | H | (Bond) | CH₂ | 2 | phenyl |
| CH₃ | CH₃ | H | O | CH₂ | 1 | phenyl |
| CH₃ | NH₂ | H | O | CH₂ | 1 | thienyl |
| CH₃ | NH₂ | H | (Bond) | CH₂ | 2 | phenyl |
| CH₃ | NH₂ | H | NH | CH₂ | 1 | phenyl |
| CH₂CN | CH₃ | H | O | CH₂ | 1 | phenyl |
| CH₂CN | CH₃ | H | NH | CH₂ | 1 | thienyl |
| CH₂CN | CH₃ | H | (Bond) | CH₂ | 2 | thienyl |
| CH₂CN | CH₃ | H | (Bond) | CH₂ | 3 | thienyl |
| CH₂CN | CH₃ | H | (Bond) | CH₂ | 3 | phenyl |
| H | NH₂ | H | (Bond) | —CH=CH—CH₂— | 1 | phenyl |

We claim:
1. A compound represented by the formulas:

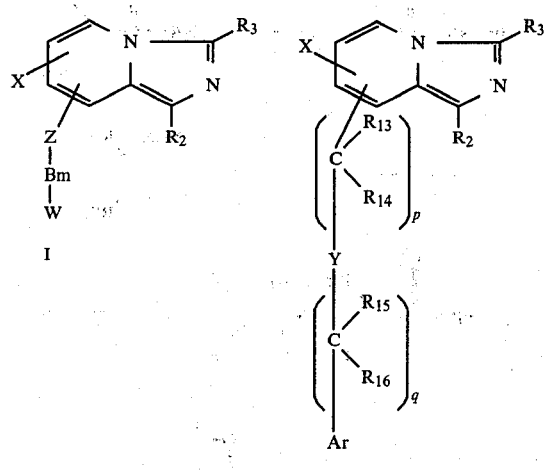

the 5,6,7,8-tetrahydro, and perhydro derivatives thereof, and the pharmaceutically acceptable salts thereof, wherein:

$R_2$ and $R_3$ each independently represent hydrogen, lower alkyl, trifluoromethyl, B-CF₃, B-Ar, carbocyclic aryl, pyridyl, halogen, B-halogen, B-OR₈, B-S(O)ₙ-lower alkyl, wherein (n) is 0,1, or

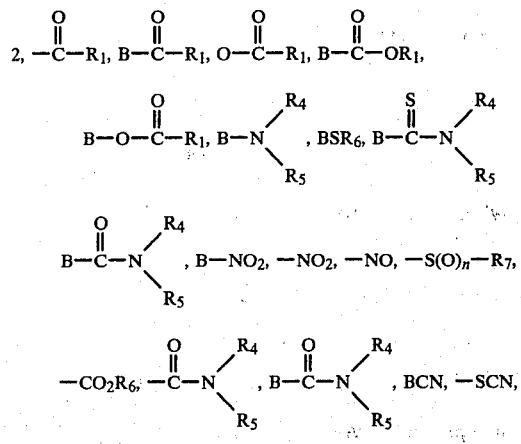

-continued

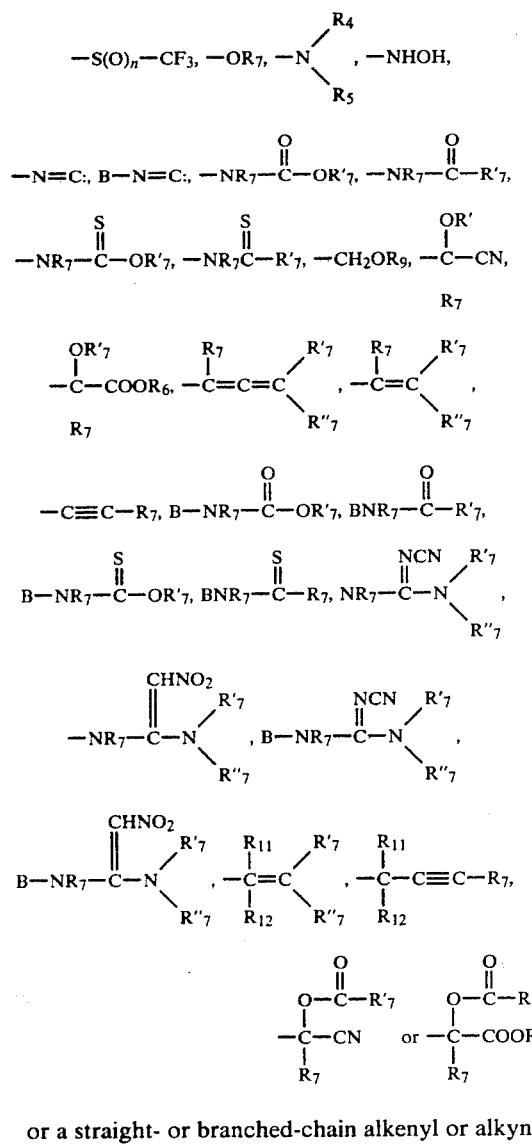

or a straight- or branched-chain alkenyl or alkynyl group having 2 to 6 bridging carbon atoms and aryl substituted derivatives thereof;

X represents hydrogen, lower alkyl, halogen, hydroxy, lower alkoxy, trifluoromethyl,

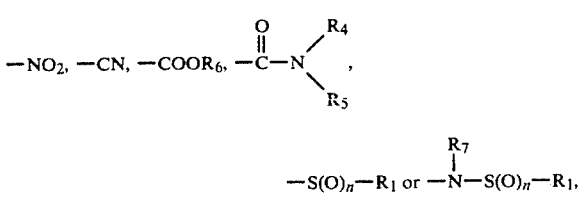

wherein n is zero, one or two with the proviso that when $R_1$ represents

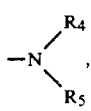

n represents two;

Z represents O, S, SO, SO$_2$, NR$_6$, or a bond connecting B to the 5-, 6-, 7-, or 8-position of the imidazo [1,5-a]pyridine nucleus;

B represents a straight-or branched-chain lower alkylene moiety;

$B_m$ represents a straight-or branched-chain lower alkylene moiety and, when Z is a bond connecting $B_m$ and the imidazo[1,5-1]pyridine nucleus, the —OR$_7$ derivatives thereof or the α(β)-or β(γ)-unsaturated derivatives thereof;

m is 1 to 10 with the proviso that when W is Ar, the number of bridging carbons between Z and W is no greater than 5;

W represents Ar wherein Ar represents phenyl, pyridyl, thienyl, imidazolyl, furanyl or X'-, Y'-, Z'-substituted-phenyl wherein each of X', Y', and Z' independently are as hereinabove defined for X; and when m is 1 to 3, W represents alkenyl, alkynyl, $Z^1R_6$ or $Z^1COR_6$ wherein $Z^1$ is S, SO, or SO$_2$;

Y represents O, S, SO, SO$_2$ or NR$_6$;

where in the above definitions:

$R_1$ represents Ar, lower alkyl,

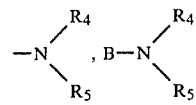

or Ar-loweralkyl;

$R_4$ and $R_5$ each independently represent hydrogen, lower alkyl, Ar, Ar-loweralkyl, loweralkoxyloweralkyl, trifluoromethylloweralkyl, or when taken together with the nitrogen atoms to which they are attached form a 4–7 membered cyclic amino or a morpholino group;

$R_6$ represents hydrogen, $C_1$- to $C_{12}$-alkyl, aryl or an aralkyl group having up to 12 carbon atoms:

$R_7$, R' and R" represent hydrogen or loweralkyl;

$R_8$ represents hydrogen, loweralkyl, loweralkoxyloweralkyl, trifluoromethylloweralkyl, Ar-loweralkyl, or Ar;

$R_9$ represents

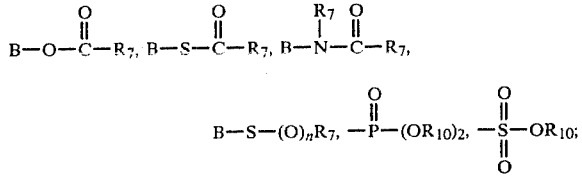

$R_{10}$ represents H, alkali metal or lower alkyl;

$R_{11}$ and $R_{12}$ each represents hydrogen or lower alkyl or together represent oxygen;

$R_{13}$ and $R_{14}$ each represent H, alkyl, aryl, or together represent —O— or —S—;

$R_{15}$ and $R_{16}$ each represent H, alkyl, aryl, or together represent —O— or —S—, provided that when $R_{13}$ and $R_{14}$ together represent —O— or —S—, $R_{15}$ and $R_{16}$ do not represent —O— or —S—;

p and q are each independently 0, 1 or 2 provided that when one of p and q is zero, the other is not zero; wherein for all variables other than W, Ar represents carbocyclic aryl.

2. A compound according to claim 1, in Formula I, wherein $R_2$ and $R_3$ each independently represents hydrogen, loweralkyl with 1 to 3 carbon atoms, —CH$_2$OH, —CH$_2$CN, —NH$_2$, —NO, CH$_2$—O—CO—R$_1$,

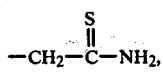

with R$_1$ representing methyl, ethyl, propyl, isopropyl, t-butyl or dimethylaminomethyl, or —S(O)$_n$—CH$_3$, with n being being zero, one or two;

X represents hydrogen;
Z represents O, NH, S or a single bond;
B represents a branched or straight chain lower alkylene group having up to 5 carbon atoms
B$_m$ represents a branched or straight chain lower alkylene group having up to 5 carbon atoms or when Z is a single bond, propenyl; and
W is allyl or Ar wherein Ar is selected from substituted phenyl, phenyl, thienyl, or pyridyl groups wherein at least one of the substituents on the phenyl group is independently selected from Cl, F, CH$_3$, t-butyl, CF$_3$, OCH$_3$, —CN and OH.

3. A compound according to claim 2 wherein in Formula I
R$_2$ and R$_3$ each independently represent H, —CH$_3$, —CH$_2$CN, —CH$_2$OH, —NH$_2$ or —NO;
X represents hydrogen;
Z is bonded to the 8 position of the imidazo[1,5-a]pyridine nucleus and represents O, NH, or a single bond;
B represents —CH$_2$—, —CH$_2$—CH$_2$—, —CH$_2$—CH$_2$—CH$_2$— or

B$_m$ represents —CH$_2$—, and when Z is a single bond, B$_m$ represents —CH$_2$CH$_2$—,

—CH$_2$—CH$_2$CH$_2$— —CH=CH—CH$_2$—; and W is Ar wherein Ar represents phenyl, o- or p-fluorophenyl, p-chlorophenyl, 2,4,6-trimethylphenyl, 2-thienyl or 3-thienyl.

4. A compound according to claim 3 wherein R$_2$ and R$_3$ each independently represent hydrogen, methyl, amino, cyanomethyl, or —CH$_2$OH;
X represents hydrogen;
Z represents O, —NH or single bond; when Z represents O or —NH, B$_m$ represents —CH$_2$—, and when Z is a single bond, B$_m$ represents —CH$_2$—CH$_2$— or —CH=CH—CH$_2$—;
B represents —CH$_2$—CH$_2$—CH$_2$—; and
W represents Ar wherein Ar is phenyl or 3-thienyl.

5. A compound of claim 4 wherein Z represents oxygen.

6. A compound of claim 4 wherein ZB$_m$W represents benzyloxy.

7. A compound of claim 4 wherein ZB$_m$W represents phenylethyl.

8. A compound of claim 4 wherein ZB$_m$W represents benzylamine.

9. A compound of claim 4 wherein ZB$_m$W represents 3-thienylmethoxy.

10. A compound of claim 4 wherein ZB$_m$W represents 3-thienylethyl.

11. A compound of claim 4 wherein ZB$_m$W represents 3-thienylmethylamino.

12. A compound of claim 4 wherein ZB$_m$W represents 3-phenyl-1-propenyl.

13. A compound of claim 4 which is 3-methyl-8-benzyloxyimidazo[1,5-a]pyridine.

14. A compound of claim 4 which is 3-methyl-8-(2-phenylethyl)imidazo[1,5-a]pyridine.

15. A compound of claim 4, which is 3-methyl-8-benzyloxyimidazo[1,5-a]pyridine-1-acetonitrile.

16. A compound of claim 1, Formula II wherein

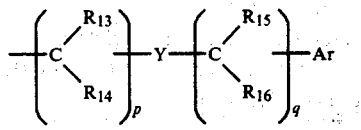

is bonded to the 8 position of the imidazo-[1,5-a]pyridine nucleus.

17. A compound of claim 16 which is an 8-phenoxymethyl compound of formula II.

18. A method for the treatment of the symptoms of peptic ulcer disease in mammals, which comprises administering to a mammal having peptic ulcer disease a therapeutically effective quantity of a compound of claim 1.

19. A method for the treatment of gastric ulcers in mammals which comprises administering to a mammal having gastric ulcers a therapeutically effective quantity of a compound of claim 1.

20. A method for the treatment of duodenal ulcers in mammals which comprises administering to a mammal having duodenal ulcers a therapeutically effective quantity of a compound of claim 1.

21. A method for inhibiting the formation of drug-induced gastrointestinal damage in mammals which comprises administering a therapeutically effective amount of a compound of claim 1 during the term said gastrointestinal damaging drug is administered for its therapeutic effect.

22. A method for the treatment of gastrointestinal damage due to stress which comprises administering to a mammal suffering from such damage a therapeutically effective quantity of a compound of claim 1.

23. A method of claim 18 which comprises administering to a mammal having peptic ulcer disease, a therapeutically effective quantity of 3-methyl-8-(2-phenylethyl)-imidazo[1,5-1]pyridine.

24. A pharmaceutical formulation for use in the treatment of ulcers which comprises a compound of claim 1 in a therapeutically effective amount sufficient to alleviate the symptoms of peptic ulcer disease together with a pharmaceutically acceptable carrier.

25. A pharmaceutical formulation of claim 24 which comprises a therapeutically effective amount of a compound represented by the formula

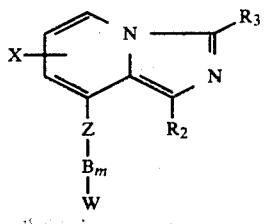

and the 5,6,7,8-tetrahydro, and perhydro derivatives thereof, and the pharmaceutically acceptable salts thereof, wherein $R_2$ and $R_3$ each independently represent H, —$CH_3$, —$CH_2CN$, $CH_2OH$, —$NH_2$ or —NO;

X represents hydrogen;

Z represents O, NH, or a single bond;

B represents —$CH_2$—, —$CH_2$—$CH_2$—, —$CH_2$—$CH_2$—$CH_2$— or $$-\underset{\underset{\text{CH}_3}{|}}{\text{CH}}-;$$

$B_m$ represents —$CH_2$—, and when Z is a single bond, $B_m$ represents

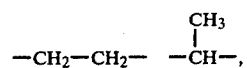

—$CH_2$—$CH_2$—$CH_2$— or —CH=CH—$CH_2$—;
and W is Ar wherein Ar represents phenyl, o- or p-fluorophenyl, p-chlorophenyl, 2,4,6-trimethylphenyl, 2-thienyl or 3-thienyl.

26. A pharmaceutical formulation of claim 25 comprising a therapeutically effective amount of 8-benzyloxy-3-methylimidazo[1,5-a]pyridine-1-acetonitrile together with a nontoxic pharmaceutically acceptable carrier.

27. A pharmaceutical formulation of claim 25 comprising a therapeutically effective amount of 8-benzyloxy-3-methylimidazo[1,5-a]pyridine together with a non-toxic pharmaceutically acceptable carrier.

28. A pharmaceutical formulation of claim 25 comprising a therapeutically effective amount of 3-methyl-8-(2-phenylethyl) imidazo[1,5-a]pyridine together with a non-toxic pharmaceutically acceptable carrier.

29. A pharmaceutical formulation of claims 24, 25, 26, 27 or 28 suitable for administration via the oral route.

* * * * *